(12) United States Patent
Lentvorski et al.

(10) Patent No.: US 12,201,736 B2
(45) Date of Patent: Jan. 21, 2025

(54) AUTOMATIC STERILIZATION AND CHARGING OF WEARABLE DEVICE (71) Applicant: Thirdwayv, Inc., Irvine, CA (US)

(72) Inventors: Andrew Lentvorski, San Diego, CA (US); James Kamke, Irvine, CA (US)

(73) Assignee: THIRDWAYV, INC., Irvine, CA (US)

( * ) Notice: Subject to any disclaimer, the term of this patent is extended or adjusted under 35 U.S.C. 154(b) by 701 days.

(21) Appl. No.: 17/277,022

(22) PCT Filed: Sep. 30, 2019

(86) PCT No.: PCT/US2019/053745
§ 371 (c)(1),
(2) Date: Mar. 17, 2021

(87) PCT Pub. No.: WO2020/076532
PCT Pub. Date: Apr. 16, 2020

(65) Prior Publication Data
US 2022/0023463 A1    Jan. 27, 2022

Related U.S. Application Data (60) Provisional application No. 62/743,702, filed on Oct. 10, 2018.

(51) Int. Cl.
A61L 2/10         (2006.01)
A61B 5/00         (2006.01)
(Continued)

(52) U.S. Cl.
CPC .............. *A61L 2/10* (2013.01); *A61B 5/6801* (2013.01); *A61L 2/24* (2013.01); *H02J 50/80* (2016.02); *A61L 2202/122* (2013.01)

(58) Field of Classification Search
CPC ........ A61L 2/10; A61L 2/24; A61L 2202/122; A61B 5/6801; H02J 50/80; H04B 1/3877;
(Continued)

(56) References Cited

U.S. PATENT DOCUMENTS 7,258,449 B2   8/2007  Chong et al.
8,576,073 B2  11/2013  Mooring et al.
(Continued)

FOREIGN PATENT DOCUMENTS

CN        104485723        1/2015

OTHER PUBLICATIONS

International Search Report and Written Opinion (mailing date Dec. 18, 2019) for International PCT Patent Application No. PCT/US2019/053745, filed Sep. 30, 2019.

*Primary Examiner* — Regina M Yoo
(74) *Attorney, Agent, or Firm* — Snell & Wilmer LLP (57) ABSTRACT Methods, systems, devices and apparatuses for sterilizing and charging a wearable device. The sterilizing and charging apparatus includes one or more light sources. The one or more light sources are configured to detect or sterilize the wearable device. The sterilizing and charging apparatus includes a wireless charging device. The wireless charging device is configured to charge the wearable device. The sterilization and charging apparatus includes a controller coupled to the one or more light sources and the wireless charging device. The controller is configured to determine, using the one or more light sources, that the wearable device is within an enclosure. The controller is configured to sterilize the wearable device using the one or more light sources and/or wirelessly charge the wearable device using the wireless charging device.

4 Claims, 5 Drawing Sheets (51) Int. Cl.
*A61L 2/24* (2006.01)
*H02J 50/80* (2016.01)

(58) Field of Classification Search
CPC .................. H04B 1/3883; H04B 1/385; H04B 2001/3855; H04B 2001/3861; H04M 1/01
See application file for complete search history.

(56) References Cited

U.S. PATENT DOCUMENTS

| | | | |
|---|---|---|---|
| 11,394,247 B1* | 7/2022 | Tsibulevskiy | H02J 7/06 |
| 2013/0294969 A1* | 11/2013 | Chen | A61B 5/14551 |
| | | | 320/108 |
| 2014/0275850 A1* | 9/2014 | Venkatraman | A61B 5/02427 |
| | | | 600/595 |
| 2014/0275884 A1* | 9/2014 | Lin | A61B 5/6838 |
| | | | 600/324 |
| 2015/0137747 A1* | 5/2015 | Salter | A61L 2/10 |
| | | | 320/108 |
| 2016/0006292 A1* | 1/2016 | Hatanaka | H02J 7/0042 |
| | | | 320/108 |
| 2016/0203698 A1* | 7/2016 | Steinbok | A47G 29/00 |
| | | | 340/521 |
| 2016/0317268 A1* | 11/2016 | Dietzel | A61C 19/02 |
| 2017/0014538 A1 | 1/2017 | Rantala | |
| 2017/0080251 A1 | 3/2017 | Yehezkel | |
| 2017/0100225 A1* | 4/2017 | Kim | A61L 2/24 |
| 2017/0358942 A1* | 12/2017 | Pugh | A61B 5/681 |
| 2018/0110959 A1 | 4/2018 | Cronin et al. | |
| 2019/0110746 A1* | 4/2019 | Dau | A61L 2/10 |
| 2020/0087031 A1* | 3/2020 | Yoo | A45D 44/00 |
| 2020/0360202 A1* | 11/2020 | Nightingale | A61B 90/90 |
| 2021/0196848 A1* | 7/2021 | Baarman | H04M 1/18 |

* cited by examiner

AUTOMATIC STERILIZATION AND CHARGING OF WEARABLE DEVICE

CROSS-REFERENCE TO RELATED APPLICATIONS

This application claims priority to and the benefit of U.S. Provisional Patent Application No. 62/743,702 titled "AUTOMATIC STERILIZATION AND CHARGING OF WEARABLE DEVICE," filed on Oct. 10, 2018, and the entirety of which is hereby incorporated by reference herein.

BACKGROUND

1. Field

This specification relates to a system, a device and/or a method for automatically sterilizing and charging a wearable device.

2. Description of the Related Art

Wearable devices are even more prevalent than ever before. Wearable devices provide various functionalities that are similar to personal devices, such as smartphones, mobile phones and other personal devices, but may be coupled to or worn by at user. The convenience of having a device on one's body that performs all the functions of a mobile device is advantageous to user's who need constant monitoring and/or are carrying multiple objects. For example, a wearable device may track the amount of exercise that a user performs, the heart rate of the user or other metrics of the user's health, actions or environmental surroundings. In another example, a doctor in a hospital may need to carry multiple items or objects, such as a patient's charts, medical supplies and/or medical devices, when working, and thus, the use of the wearable device allows the doctor to move about without the need to carry a mobile device. Moreover, the doctor may be more accurately located when wearing the wearable device because the wearable device is coupled to the doctor's body.

However, as wearable devices become more ubiquitous and are introduced into different environments, which expose the wearable devices to the elements, these wearable devices will require maintenance and cleaning between use. Accordingly, there is a need for a system, an apparatus, a method and/or a device that automatically sterilizes and charges the wearable device.

SUMMARY

In general, one aspect of the subject matter described in this specification is embodied in a device, a system and/or an apparatus for automatically sterilizing and charging a wearable device. The sterilization and charging system includes a sterilization and charging apparatus. The sterilizing and charging apparatus includes one or more light sources. The one or more light sources are configured to detect or sterilize the wearable device. The sterilizing and charging apparatus includes a wireless charging device. The wireless charging device is configured to charge the wearable device. The sterilization and charging apparatus includes a controller coupled to the one or more light sources and the wireless charging device. The controller is configured to determine, using the one or more light sources, that the wearable device is within an enclosure. The controller is configured to sterilize the wearable device using the one or more light sources and/or wirelessly charge the wearable device using the wireless charging device.

These and other embodiments may optionally include one or more of the following features. The one or more light sources may include an ultraviolet (UV) light source that is configured to emit UV rays to sterilize the wearable device. The UV rays may be directed at the wearable device from multiple directions and may be either continuous or time-varied. The controller may be configured to control or adjust a level of power or intensity of the one or more light sources or a level of power of the wireless charging device.

The sterilization and charging. apparatus may include a memory. The memory may be configured to store a profile for each category of multiple categories of different wearable devices. The profile may indicate a level of power or intensity for the one or more light sources or a level of power of the wireless charging device. The controller may be configured to determine light characteristics of the wearable device using the one or more light sources. The controller may be configured to determine a category associated with the wearable device based on the light characteristics. The controller may be configured to sterilize or wirelessly charge the wearable device based on the profile.

The sterilization and charging apparatus may include a display. The display may be configured to display status information related to sterilization, charging or data communication with the wearable device. The sterilization and charging apparatus may include a power source for providing power. The wireless charging device may be a wireless transmitter that wirelessly transmits a wireless charging signal. To wirelessly charge the wearable device, the controller may be configured to determine a level of power of the wireless charging signal, determine a direction of the wireless charging signal, and emit the wireless charging signal to wirelessly charge a battery of the wearable device or operate the wearable device. The wireless transmitter may be configured to emit the wireless charging signal so that the wireless charging signal surrounds the wearable device.

The controller may be configured to connect with the wearable device. The controller may be configured to download data from a memory of the wearable device. The controller may be configured to provide or transmit the downloaded data to at least one of a personal device, a server or a remote storage via a wireless or a wired connection.

The one or more light sources may be configured to detect and sterilize the wearable device. The controller may be configured to determine a baseline level of an ultraviolet signal with the enclosure. The controller may be configured to determine a current level of the UV signal within the enclosure. The controller may he configured to determine that the wearable device is within the enclosure when the current level is different than the baseline level due to interference within the enclosure from introduction of the wearable device.

The sterilization and charging apparatus may include multiple light detectors. The multiple light sources or the multiple light detectors may be positioned around and within a cavity of the enclosure to surround the wearable device to optimize exposure of the wearable device to emitted light. The one or more light sources may emit an ultraviolet light, radio frequency or visible light and emit different levels of intensities of the ultraviolet light, the radio frequency or the visible light when detecting and/or sterilizing the wearable device.

In another aspect, the subject matter is embodied in a sterilization and charging system. The sterilization and charging system includes an enclosure. The enclosure is configured to surround or enclose a wearable device. The enclosure has multiple walls with a coating that reflects, refracts or redirects light. The sterilization and charging system includes one or more light sources. The one or more light sources are configured to emit light to detect or sterilize the wearable device. The sterilization and charging system includes a wireless charging device. The wireless charging device is configured to charge the wearable device. The sterilization and charging system includes a controller. The controller is coupled to the one or more light sources and the wireless charging device. The controller is configured to determine, using the one or more lights sources, that the wearable device is within the enclosure. The controller is configured to sterilize the wearable device using the one or more light sources or wirelessly charge the wearable device using the wireless charging device.

In another aspect, the subject matter is embodied in a method for sterilizing or charging a device. The method includes detecting a device within an enclosure using a light having a first intensity from a light source. The method includes sterilizing the device using the light with a second intensity from the light source. The method includes wirelessly charging the device using a wireless charging signal.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale and may be exaggerated to better illustrate the important features of the present invention. In the drawings, like reference numerals designate like parts throughout the different views.

DETAILED DESCRIPTION

Disclosed herein are systems, apparatuses, devices and methods for automatically sanitizing, charging and/or communicating, with a wearable device, such as a wearable smart device. The wearable smart device sterilization and charging system ("sterilization and charging system") cleans, sanitizes, sterilizes, charges and/or otherwise maintains a wearable smart device ("wearable device"). The wearable device may be a medical device, smart device or other personal device coupled to or worn on the body of a user. For example, the wearable device may be used for drug delivery, continuous positive airway pressure (CPAP) therapy, communication gateways, etc. In another example, the wearable device may be a sensor or other medical device, such as an insulin pump, a blood pressure meter, a glucose meter, a heart rate monitor, a pulse oximeter, an orthopedic brace or manipulation device, and/or a dental brace or other orthodontic brace or device.

The sterilization and charging system encloses or otherwise surrounds the wearable device so that the sterilization and charging system may sanitize, sterilize or otherwise clean the surfaces of the wearable device to reduce or eliminate foreign particulates. The sterilization and charging system eliminates, kills or otherwise removes particulates, germs and other microorganisms, such as fungi, bacteria, viruses, spores or other biological agents present on the surface and/or within the wearable device. This is particularly important to prevent, reduce or otherwise eliminate cross-contamination in a hospital or research facility, for example.

Other benefits and advantages include that the sterilization and charging system may establish a connection with the wearable device to charge the wearable device and/or communicate with the wearable device. The sterilization and charging system may provide electrical power to the wearable device to charge the power storage device of the wearable device. The sterilization and charging system may provide the electrical power via a wireless or a wired connection. This allows the sterilization and charging system to simultaneously charge and sterilize the wearable device. Additionally, the sterilization and charging system may initialize or reinitialize a wearable device for reuse. The sterilization and charging system may access, download and/or purge data from the wearable device to allow the wearable device to be reused.

Figure 1:
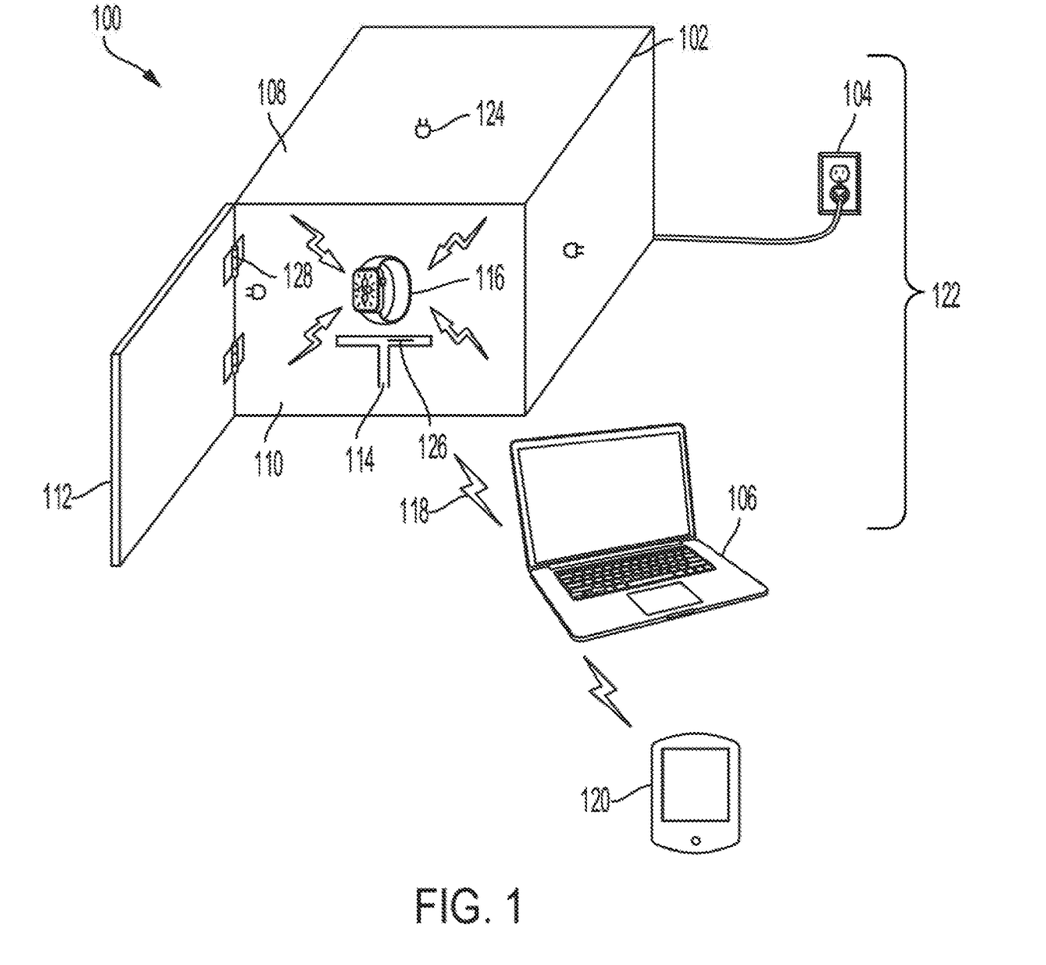
FIG. 1 shows an example sterilization and charging system according to an aspect of the invention.

FIG. 1 shows a sterilization and charging system 100. The sterilization and charging system 100 includes a sterilization and charging apparatus 122. The sterilization and charging system 100 may include a wearable device 116. The wearable device 116 may be a medical device, smart device or other personal device coupled to or worn on the body of a user. The sterilization and charging system 100 may have a remote device 120 and/or a network 118 that links the sterilization and charging apparatus 122, the wearable device 116 and/or the remote device 120.

The remote device 120 may be a personal device, such as a laptop, a tablet, a smartphone or another computing device, a server, a database and/or another storage device. The network 118 may be a Dedicated Short-Range Communication (DSRC) network, a local area network (LAN), a wide area network (WAN), a cellular network, the Internet, or combination thereof, that connects, couples and/or otherwise communicates among the sterilization and charging apparatus 122, the wearable device 116 and/or the remote device 120.

The sterilization and charging apparatus 122 detects when the wearable device 116 is placed within and ready for sterilization. The sterilization and charging apparatus 122 may configure the intensity, amount or level of the sterilization and/or charging of the wearable device 116 so that no damage occurs to the wearable device 116 when sterilizing or charging the wearable device 116. Moreover, the sterilization and charging apparatus 122 may position, move, direct or otherwise control the relative direction of signals to sterilize, charge, clean or detect the wearable device 116.

Figure 2:
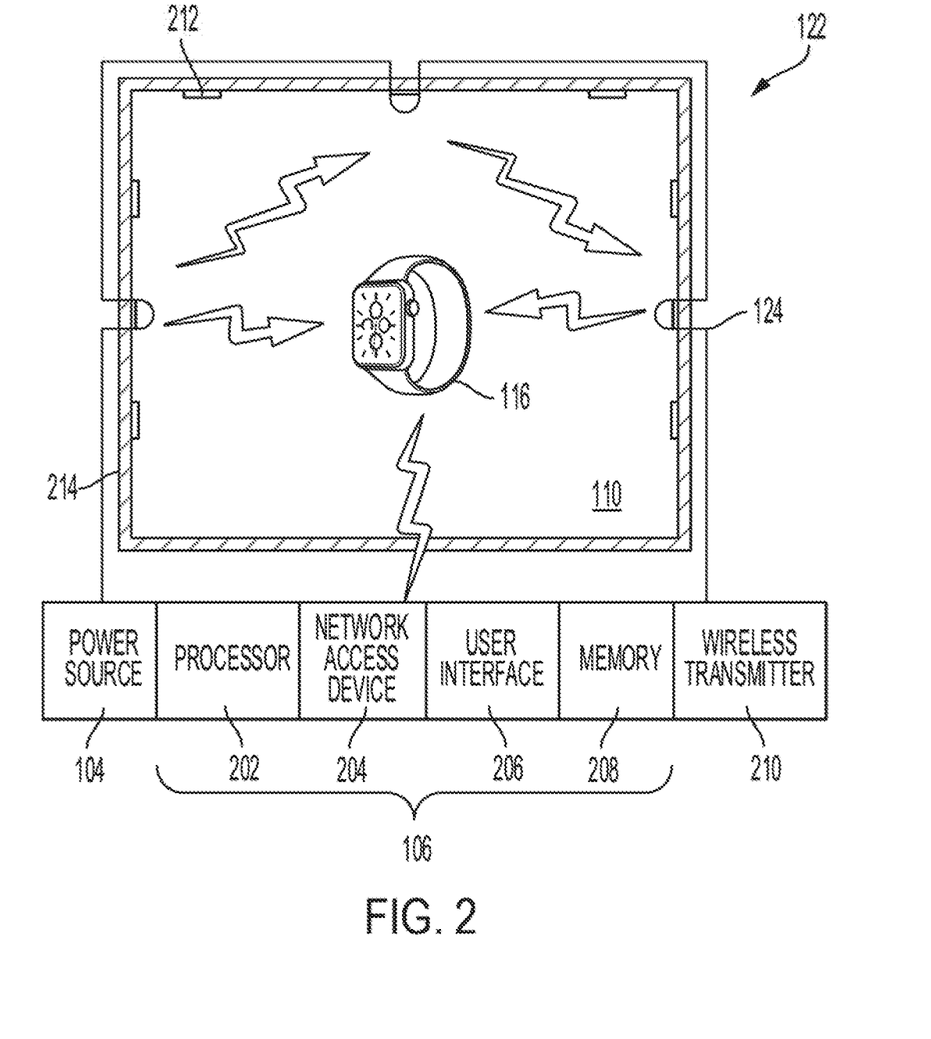
FIG. 2 is a block diagram of an example sterilization and charging apparatus of the sterilization and charging system of FIG. 1 according to an aspect of the invention.

The sterilization and charging apparatus 122 includes an enclosure 102 or other container, a power source 104, a computing device 106 or other controller, and/or one or more light sources 124, as shown in FIGS. 1-2 for example. The sterilization and charging apparatus 122 may include one or more sensors 212. The enclosure 102 has multiple walls 108 that are arranged to surround, enclose, form and/or define a cavity 110 within. The enclosure 102 has a lid or door ("lid") 112, which may be opened or closed to allow access to the cavity 110 within the enclosure 102. For example, the lid 112 may be connected to a hinge 128 or other fastener, which may be coupled to an edge of one of the multiple wails 108. The hinge 128 may allow the lid 112 to be moved, placed or otherwise positioned into the open or closed position to allow or deny access to the cavity 110 within the enclosure 102. When the lid 112 is open, the wearable device 116 may be placed within the cavity 110 of the enclosure 102. The enclosure 102 may have a platform 114 or other holder. The platform 114 may be positioned within the cavity 110 and may be coupled, fastened or otherwise configured to receive the wearable device 116 to hold the wearable device 116. The platform 114 may have a data/charging port 126, which may be used to couple the wearable device 116 with the computing device 106 and or the power source 104 to communicate with and/or power the wearable device 116. For example, the wearable device 116 may connect to the data/charging port 126 of the platform 114 to send or receive communication and/or receive electrical power via the platform 114.

In some implementations, the platform 114 may be rotatable or movable within the cavity 110 of the enclosure 102. The platform 114 may be rotatable or movable to rotate or otherwise move the wearable device 116, which may be fixed of the platform 114. This provides more exposure of the surfaces of the wearable device 116 to light or other signals emitted within cavity 110 or may more efficiently direct or position a wireless charging signal to be received by the wearable device 116.

FIG. 2 shows a block diagram of the sterilization and charging apparatus 122. The enclosure 102 may have a coating 214. The coating 214 may be a layer or thin film of coating 214 placed, molded or otherwise covering an inner surface of the multiple walls 108. The coating 214 may reflect, refract or redirect any emitted signals, light or other radiation inward into the cavity 110 to surround a wearable device 116 placed or positioned within the cavity 110.

The sterilization and charging apparatus 122 may have one or more sensors 212. The one or more sensors may include an ultraviolet (UV) light detector, a radio frequency (RF) detector or a camera. The one or more sensors 212 may include multiple sensors positioned throughout the walls of the enclosure 102 to detect changes in the UV environment. The one or more sensors 212 may detect the amount or intensity of the light or wireless charging signal being emitted and/or may detect the presence or lack of presence of the wearable device 116. Moreover, the one or more sensors 212 may identify the type or category of the wearable device 116 placed within the cavity 110 and/or whether the lid 112 is open or closed.

The sterilization and charging apparatus 122 has one or more light sources 124. The one or mom light sources 124 may be positioned within the multiple walls 108 so that when light or other signal is emitted from the one or more light sources 124 the light or other signal may surround the wearable device 116. The one or more light sources 124 may include multiple light sources 124. The multiple light sources 124 may positioned to surround the wearable device 116. This optimizes the exposure of the surfaces of the wearable device 116 to the emitted light.

The one or more light sources 124 may emit an ultraviolet (UV) light, radio frequency, visible light or other signal (hereinafter, interchangeably referred to as "light" or "signal") to detect and/or sterilize the wearable device 116. The emitted light may be continuous or time-varying. The sterilization and charging apparatus may control the direction and/or intensity of the emitted light when detecting and/or sterilizing the wearable device 116 to optimize exposure of the wearable device 116 to the emitted light.

The sterilization and charging apparatus 122 has a computing device 106. The computing device 106 includes a processor 202, a network access device 204, a user interface 206 and/or a memory 208. The computing device 106 may include a wireless transmitter 210 or the wireless transmitter 210 may be a separate and distinct device.

The processor 202 may be implemented as a single processor or controller as multiple processors and/or controllers. The processor 202 may be electrically coupled to the other components and may be designed to control the one or more light sources 124, the wireless transmitter 210 and/or the power source 104. The processor 202 may control the intensity and/or direction of the emitted signal or light from the one or more lights sources 124 and/or the wireless transmitter 210. The processor 202 may cause the display of notification or alerts on the user interface 206 to notify, alert or otherwise inform a user of the status of the sterilization and/or charging of the wearable device 116. The processor 202 may he coupled to the memory 208 and execute instructions that are stored in the memory 208.

The memory 208 may be coupled to the processor 202, and store instructions that the processor 202 executes. The memory 208 may store profiles of different types or categories of wearable devices. The profiles may indicate different configurations or requirements of the wearable device 116, such as hardware limitations of the wearable device 116 including rates of power transfer. The memory 208 may include one or more of a Random Access Memory (RAM), Read Only Memory (ROM) or other volatile or non-volatile memory. The memory 208 may be a non-transitory memory or a data storage device, such as a hard disk drive, a solid-state disk drive, a hybrid disk drive, or other appropriate data storage, and may further store machine-readable instructions, which may be loaded and executed by the processor 202.

The computing device 106 has a user interface 206. The sterilization and charging apparatus 122 may receive user input via the user interface 206. The user input may include the level or intensity of the wireless charging signal or the emitted light from the one or more light sources 124. The user input may include an indication of when to begin sterilization and/or wireless charging.

The user interface 206 may include in input/output device that receives user input from a user interface element, a button, a dial, a microphone, a keyboard, or a touch screen. The user interface 206 may provide an output to an output device, such as a display, a speaker, an audio and/or visual indicator, or a refreshable braille display. The output device may display an alert or notification to the user.

The computing device 106 includes, a network access device 204. The network access device 204 may include a communication port or channel, such as one or more of a Dedicated Short-Range Communication (DSRC) unit, a Wi-Fi unit, a Bluetooth® unit, a radio frequency identification (RFID) tag or reader, or a cellular network unit for accessing a cellular network (such as 3G, 4G or 5G). The network access device 204 may transmit data to and receive data from the different components of the sterilization and charging system 100 including the platform 114 via the data/charging port 126, the wearable device 116 and/or the remote device 120. For example, the processor 202 may download data from the wearable device 116 either wirelessly or via the platform 114 and data/charging port 126 and may upload the downloaded data to the remote device 120 for storage. In another example, the computing device 106 may send commands to control the one or more light sources 124 and/or receive sensor data from the one or more sensors 212 to detect the wearable device 116.

The sterilization and charging apparatus 122 has a power source 104 and/or a wireless transmitter 210. The power source 104 may be a portable power device, such as a battery, or may be a fixed power device, such as an electrical socket. The power source 104 provides power to the sterilization and charging apparatus 122. The power source 104 may be coupled to the data/charging port 126 to power or charge the wearable device 116 when the wearable device 116 is fixed to the platform 114 and connected to the data/charging port 126. Moreover, the power source 104 may provide power to the wireless transmitter 210 to send a wireless charging signal.

The wireless transmitter 210 may transmit or emit a wireless charging signal to the wearable device 116. The wireless charging signal may charge or otherwise power the wearable device 116 with an electrical charge. The wireless charging signal may be a high frequency alternating electromagnetic field, such as a magnetic field generated using an alternating current (AC), which is transmitted to the wearable device 116 and converted into an electrical charge, such as into direct current (DC), that is used to charge, power and/or store the power storage device of the wearable device 116.

Figure 3:
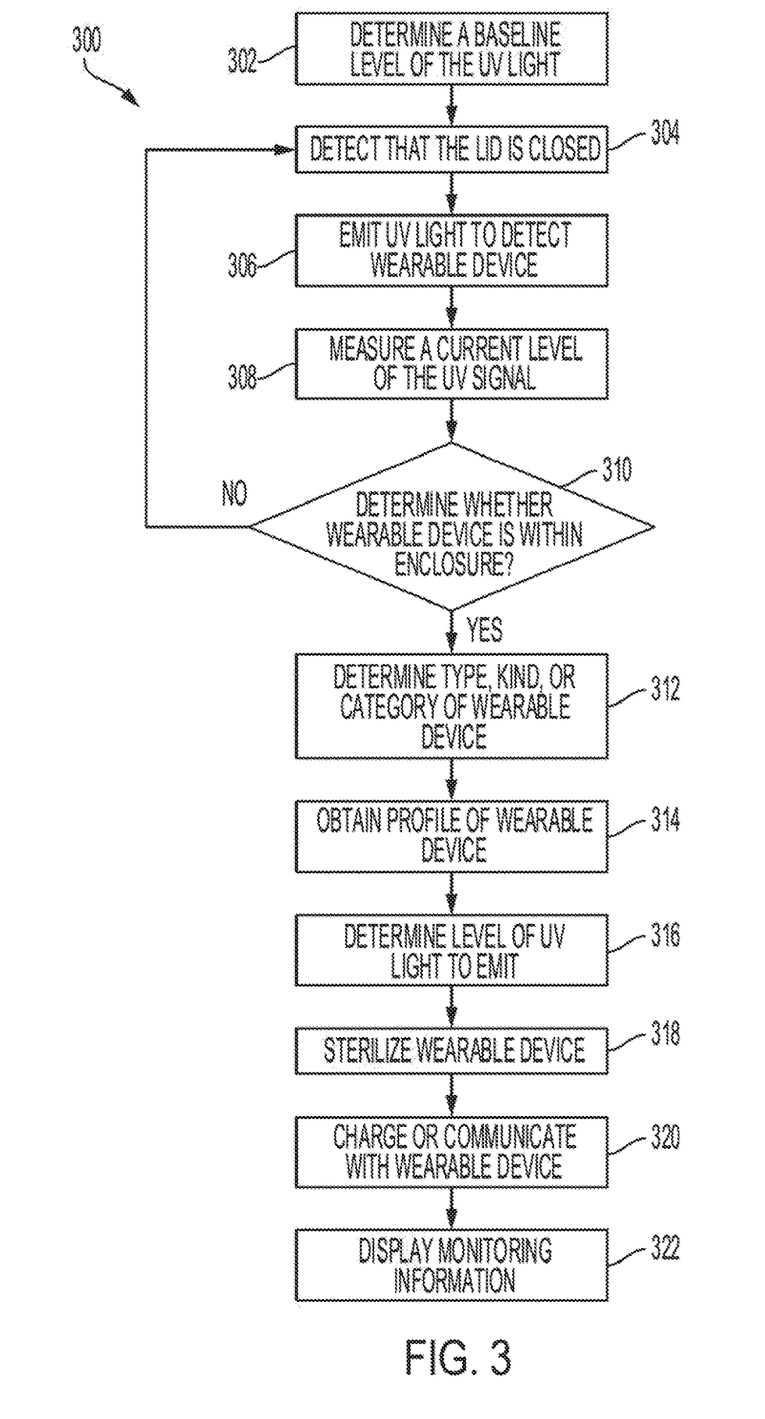
FIG. 3 is a flow diagram of an example process for sterilizing the wearable device using the sterilization and charging system of FIG. 1 according to an aspect of the invention.

FIG. 3 is a flow diagram of an example process 300 for sterilizing the wearable device 116. One or more computers or one or more data processing apparatuses, for example, the processor 202 of the sterilization and charging system 100 of FIG. 1 appropriately programmed, may implement the process 300.

The sterilization and charging apparatus 122 may determine a baseline level of the ultraviolet (UC) light within the cavity 110 of the enclosure 102 (302). Different signals may be used instead of the UV light to detect and/or sterilize the wearable device 116. For example, other signals that may be used include a radio frequency signal, visible light, or other type or kind of signal.

The sterilization and charging apparatus 122 may use one or more sensors 212, such as a UV light detector, to capture or determine the baseline level of the UV light when the wearable device 116 is not within the cavity 110 of the enclosure 102. The one or more light sources 124 may be activated to transmit UV light throughout the cavity 110 of the enclosure 102 when the wearable device 116 is known to be not within the cavity 110, and the one or more sensors 212 may measure the amount of UV light within the cavity 110 to establish the baseline level of UV light. The baseline level of the UV light may be stored within the memory 208 for comparison with a measured level of a UV light to determine the presence or lack of presence of the wearable device 116.

The sterilization and charging apparatus 122 may determine that the lid 112 of the enclosure 102 is closed prior to sterilization and/or wireless charging (304). The sterilization and charging apparatus 122 may use one or more sensors 212 to determine whether the lid 112 is ajar, i.e., in an open or partially open position. When the lid 112 is ajar and not in the closed position, the sterilization and charging apparatus 122 may prevent the wireless charging and/or sterilization of the wearable device 116 from activating, such as electrically disconnecting or de-coupling power to the one or more light sources 124 and/or the wireless transmitter 210. This prevents unintended signals, such as UV light and/or wireless charging signals, from unintentionally emanating from the enclosure 102 and exposing the user. When the lid 112 is in the closed position, the sterilization and charging apparatus 122 may allow the activation of the wireless charging and/or sterilization of the wearable device 116.

Once the lid 112 is closed, the sterilization and charging apparatus 122 may emit a UV light (306). The emitted UV light may be used to detect the wearable device 116 within the cavity 110 of the enclosure 102. The emitted UV light used to detect the wearable device 116 may have a different intensity than the emitted UV light used to sterilize the wearable device.

The sterilization and charging apparatus 122 may measure a current level of the UV light within the cavity 110 of the enclosure 102 (308). The sterilization and charging apparatus 122 uses one or more sensors 212 to measure the current level of the UV light within the cavity 110. For example, a UV light detector may measure level of the UV light within the cavity 110.

The sterilization and charging apparatus 122 determines whether the wearable device 116 is within the enclosure 102 (310). The sterilization and charging apparatus 122 may compare the current level of the UV light with the baseline level of the UV light and determine a difference between the current level and the baseline level. If the difference between the current level and the baseline level is greater than a threshold amount, the sterilization and charging apparatus 122 may determine that the wearable device 116 is present within the enclosure 102. If the difference between the current level and the baseline level is less than or equal to the threshold amount, the sterilization and charging apparatus 122 may determine that the wearable device is not present within the enclosure 102.

In some implementations, the sterilization and charging apparatus 122 may use another sensor, such as a camera, to capture image data within the cavity 110 of the enclosure 102. The sterilization and charging apparatus 122 may analyze the captured image data to determine whether the wearable device 116 is within the cavity 110 of the enclosure 102.

When the sterilization and charging apparatus 122 does not detect the wearable device 116 within the enclosure 102, the sterilization and charging apparatus 122 continues to monitor the cavity 110 of the enclosure 102 for the wearable device 116. When the sterilization and charging apparatus 122 detects the wearable device 116 within the enclosure, the sterilization and charging apparatus 122 proceeds with the sterilization process.

The sterilization and charging apparatus 122 may determine the type, kind or category of the wearable device 116 (312). The sterilization and charging apparatus 122 may receive user input via the user interface 206 that indicates that type, kind or category of the wearable device 116 placed or positioned within the cavity 110 of the enclosure 102. The type, kind or category of the wearable device 116 may affect charging and/or sterilization characteristics, such as the rate or intensity, of the emitted signal that detects, charges and/or sterilizes the wearable device 116.

In some implementations, the sterilization and charging apparatus 122 measures light characteristics of the wearable device 116. The sterilization and charging apparatus 122 may use one or more sensors 212 to measure the light characteristics. The light characteristics may include the direction or the amount of light that is reflected, refracted or otherwise directed away from the surface of the wearable device 116. The sterilization and charging apparatus 122 may determine the type, kind or category of the wearable device 116 from the light characteristics because each different type, kind or category of wearable device 116 has different light characteristics. In some implementations, the sterilization and charging apparatus 122 uses one or more sensors 212, such as a camera, to capture image data, and analyzes the captured image data to determine the type, kind or category of the wearable device 116.

The sterilization and charging apparatus 122 may obtain a profile of the wearable device 116 (314). The sterilization and charging apparatus 122 may obtain the profile from the memory 208. The profile that is to he obtained may be based on and specific to the type, kind or category of the wearable device 116. For example, if the wearable device 116 is a medical device, the profile may he specific to the medical device. In another example, if the wearable device 116 is a smartwatch, the profile may be specific to the smartwatch.

The profile for a specific wearable device indicates the various charging, data communication and/or sterilization characteristics of the wearable device 116. The charging characteristics may include a rate of charge, the current and/or voltage to charge the wearable device 116 and/or an overall amount of charge that the wearable device 116 may store. The data communication characteristics may include data rates for uploading and/or downloading data to and from the wearable device 116. The sterilization characteristics may include any hardware limitations of components of the wearable device 116 that may be affected by the UV light or other signals used to sterilize the wearable device 116. Moreover, the sterilization characteristics may include a geometry of the surfaces of the wearable device 116, which may indicate the area and/or shape of the surfaces of the wearable device 116 that need to be sterilized.

The sterilization and charging apparatus 122 may determine the amount or level of intensity of the UV light to emit to sterilize the wearable device 116 (316). The amount or level of the intensity of the UV light may be pre-configured or based on the profile of the type, kind or category of the wearable device 116. For example, when the profile indicates that the wearable device is a smartwatch in comparison to a smart necklace, the amount or level of intensity of the UV light emitted to sterilize the smartwatch may be less than the amount or level of intensity of the UV light emitted to sterilize the smart necklace.

The sterilization and charging apparatus 122 may also emit different levels of intensities for the UV light for different functions. For example, when detecting the wearable device 116, the sterilization and charging apparatus 122 emits a UV light with a lower intensity than when the sterilization and charging apparatus 122 emits the UV light to sterilize the wearable device 116.

In some implementations, the sterilization and charging apparatus 122 may vary the amount or level of intensity of the UV light based on the amount of particulates on the surface of the wearable device 116. The sterilization and charging apparatus 122 may measure light characteristics of the various surfaces of the wearable device 118 and determine the amount of particulates on the various surfaces based on the light characteristics. For example, if a surface reflects or refracts more light than another surface, then the surface may have less particulates than the other surface.

Then, the sterilization and charging, apparatus 122 may adjust or determine amount or level of intensity of the UV light based on the amount of particulates. If there are more particulates, then the sterilization and charging apparatus may increase the amount or level of intensity of the signal. Similarly, if there are less particulates, then the sterilization and charging apparatus 122 may decrease the amount or level of intensity of the UV light.

The amount or level of intensity of the UV light may further vary based on the portion of the surface of the wearable device 116 where the emitted light is focused. For example, on a first portion of the wearable device 116, the sterilization and charging apparatus 122 may use a low amount or level of intensity of the UV light and a high amount or level of intensity of the UV light on a second portion of the wearable device 116.

The sterilization and charging apparatus 122 sterilizes the wearable device 116 (318). The sterilization and charging apparatus 122 may activate the one or more light sources 124 and emit the UV light or other signal to sterilize the wearable device 116. The one or more lights sources 124 may be adjusted to emit the determined amount or level of intensity of the UV light.

Figure 4:
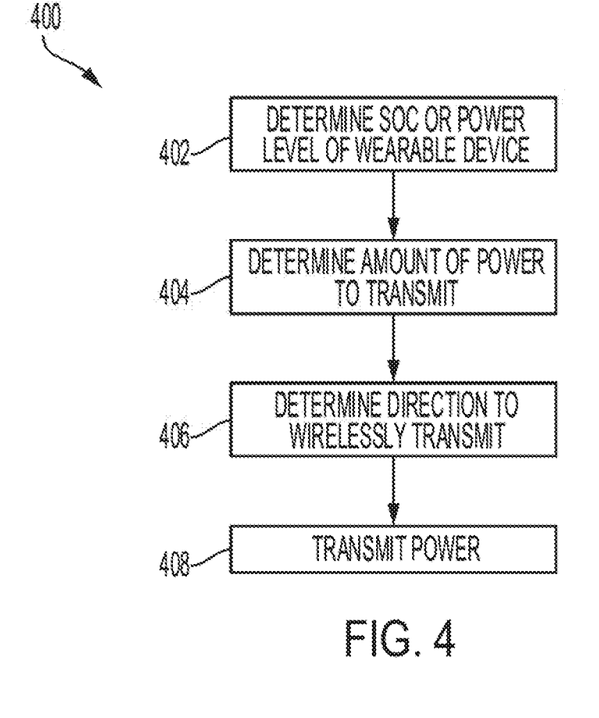
FIG. 4 is a flow diagram of an example process for charging the wearable device using the sterilization and charging system of FIG. 1 according to an aspect of the invention.
Figure 5:
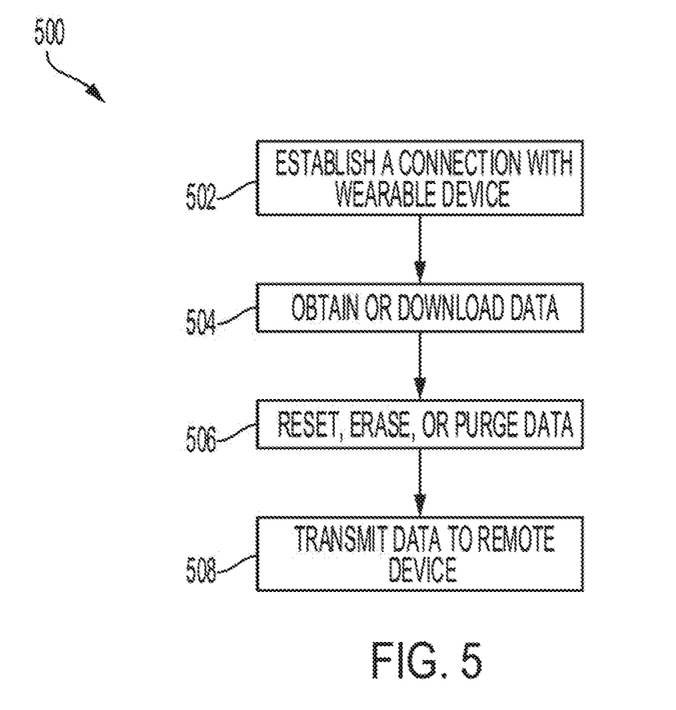
FIG. 5 is a flow diagram of an example process for communicating with the wearable device using the sterilization and charging system of FIG. 1 according to an aspect of the invention.

The sterilization and charging apparatus 122 may perform other functions, such as charging and/or data communication (320). FIGS. 4-5 further describe the processes 400 and 500 for charging and/or data communication with the wearable device 116.

Before, during or after sterilization, charging and/or data communication, the sterilization and charging apparatus 122 may display monitoring information (322). The sterilization and charging apparatus 122 may display monitoring information on the user interface 206. The monitoring information may include status information regarding the sterilization, charging and/or data communication.

For example, status information during sterilization may indicate a percentage or amount of the total surface of the wearable device 116 that has been sterilized or exposed to the UV light, a current progress of the sterilization procedure, a level of intensity of the UV light that is being emitted or other pertinent information regarding the sterilization procedure. In another example, status information related to charging of the wearable device 116 may include a current state of charge of the wearable device 116, an estimated time to completion to fully charge the wearable device, and/or a current progress of the charging procedure. In another example, status information for the data communication with the wearable device 116 may include a current download/upload rate, a current progress of downloading data from the wearable device 116 and/or an indication of when data has been purged or deleted from the wearable device 116. Other information that may be displayed include the downloaded data from the wearable device 116.

FIG. 4 is a flow diagram of an example process 400 for charging the wearable device 116. One or more computers or one or more data processing apparatuses, for example, the processor 202 of the sterilization and charging system 100 of FIG. 1, appropriately programmed, may implement the process 400.

Once the sterilization and charging apparatus 122 determines that the lid 112 of the enclosure 102 is closed and that the wearable device 116 is within the enclosure 102, the sterilization and charging apparatus 122 may determine the state of charge or power level of the wearable device 116 (402). The sterilization and charging apparatus 122 may receive an indication of the state of charge or the power level from the wearable device 116 via the data/charging port and/or wirelessly via the network access device 204.

When the state of charge or the power level is not full or above a threshold amount, the sterilization and charging apparatus 122 may determine the amount of power to transmit or provide to the wearable device 116 (404). The amount of power may be based on the profile of the wearable device 116, a default setting or configuration and/or a user-configured amount. For example, a smartwatch, a smart necklace, a medical device or other wearable device all have different charging characteristics, such as voltage, amperage or other electrical characteristic, which may be determined from the profile of the wearable device 116.

The sterilization and charging apparatus 122 may determine a direction to wirelessly transmit a wireless charging signal to the wearable device 116 when the wearable device 116 is not affixed to or coupled to a data/charging port 126 (406). The sterilization and charging apparatus 122 may emit the wireless charging signal and determine where the wireless charging signal is most efficiently received by the wearable device 116, e.g., where the wireless charging signal is most efficiently converted into electrical energy to power or charge the wearable device 116.

The sterilization and charging apparatus 122 emits or transmits power to the wearable device 116 (408). The sterilization and charging apparatus 122 may transmit the power via a wired connection from the power source 104 to the data/charging port 126 when the wearable device 116 is affixed to a platform 114 within the enclosure 102. The sterilization and charging apparatus 122 may transmit the power via a wireless connection when the wearable device 116 is not affixed to the platform 114 or there is no data/charging port 126. The transmitted power may be based on the determined amount of power to transmit.

The sterilization and charging apparatus 122 may wirelessly transmit a wireless charging signal to the wearable device 116 using the wireless transmitter 210. The wireless charging signal may be directed toward the direction that most efficiently charges the wearable device 116 and at the determine amount of power. In some implementations, the sterilization and charging apparatus 122 may move, steer or otherwise position the platform 114 where the wearable device 116 is held or placed so that the wireless charging signal may be most efficiently converted into electrical energy. In other implementations, the sterilization and charging apparatus 122 may move, steer or otherwise position the wireless transmitter 210 so that the wireless charging signal may be most efficiently converted into the electrical energy.

FIG. 5 is a flow diagram of an example process 500 for communicating with the wearable device 116. One or more computers or one or more data processing apparatuses, for example, the processor 202 of the sterilization and charging system 100 of FIG. 1 appropriately programmed, may implement the process 500.

Once the sterilization and charging apparatus 122 determines that the lid 112 of the enclosure 102 is closed and that the wearable device 116 is within the enclosure 102, the sterilization and charging apparatus 122 may establish a connection with the wearable device 116 (502). The sterilization and charging apparatus 122 may automatically establish a wireless connection with the wearable device 116 when there is no data/charging port 126. The data connection signal used to wirelessly connect with the wearable device 116 may he the same or different from the wireless charging signal. When there is a data/charging port 126, the sterilization and charging apparatus 122 may receive an indication that the wearable device 116 has connected to the data/charging port 126 and establish the connection with the wearable device 116 after receiving the indication.

The sterilization and charging apparatus 122 obtains or downloads data from the memory of the wearable device 116 (504). The sterilization and charging apparatus may download the data as part of the sterilization process and/or as a separate process. The sterilization and charging apparatus 122 downloads the data via the wired or wireless connection and may store the downloaded data in the memory 208.

The sterilization and charging apparatus 122 may reset, erase, purge or otherwise cause the data to be deleted from the memory of the wearable device 116 after the data has been downloaded (506). This allows the wearable device 116 to he completely reset to allow for reuse by another user. The sterilization and charging apparatus 122 may then send or transmit the downloaded data to a remote device 120 (508). The remote device may be a remote or cloud storage device or another device of the user, such as a personal device. The downloaded data may be transmitted via the network 118 using the network access device 204.

Where used throughout the specification and the claims, "at least one of A or B" includes "A" only, "B" only, or "A and B." Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. An apparatus for sterilizing and charging a wearable device, comprising:
   one or more light sources;
   a wireless charging device configured to charge the wearable device; and
   a controller coupled to the one or more light sources and the wireless charging device and configured to:
      determine, using the one or more light sources, that the wearable device is within an enclosure; and
      sterilize the wearable device using the one or more light sources; or
      wirelessly charge the wearable device using the wireless charging device, and
   wherein the controller is further configured to:
   determine a baseline level of an ultraviolet light within the enclosure;
   determine a current level of the ultraviolet light within the enclosure; and
   determine that the wearable device is within the enclosure when the current level is different than the baseline level due to interference within the enclosure from introduction of the wearable device.

2. An apparatus for sterilizing and charging a wearable device, comprising:
   one or more light sources;
   a wireless charging device configured to charge the wearable device;
   a controller coupled to the one or more light sources and the wireless charging device and configured to:
      determine, using the one or more light sources, that the wearable device is within an enclosure;

sterilize the wearable device using the one or more light sources; and wirelessly charge the wearable device using the wireless charging device; and a plurality of light detectors, wherein the one or more light sources or the plurality of light detectors are positioned around and within a cavity of the enclosure to surround the wearable device to optimize exposure of the wearable device to emitted light.

3. An apparatus for sterilizing and charging a wearable device inside an enclosure, the apparatus comprising:

an ultraviolet light source configured to detect and sterilize the wearable device inside the enclosure, the enclosure configured to hold the wearable device during the detecting and during the sterilizing;

a wireless charging device configured to charge the wearable device inside the enclosure; and a controller coupled to the ultraviolet light source and the wireless charging device and configured to:

determine, using the ultraviolet light source emitting light at a first intensity, that the wearable device is within the enclosure, and sterilize the wearable device using the ultraviolet light source emitting light at a second intensity, the second intensity being greater than or equal to the first intensity, and wirelessly charge the wearable device using the wireless charging device simultaneously with the sterilizing;

a memory configured to store a profile for each category of a plurality of categories of different wearable devices, wherein the profile indicates a level of intensity for the ultraviolet light source and a level of power of the wireless charging device;

wherein the controller is further configured to:

determine light characteristics of the wearable device using the ultraviolet light source wherein the light characteristics comprise a direction or an amount of ultraviolet light that is reflected by the wearable device, determine a category of the wearable device based on comparing the light characteristics to stored profiles of different wearable devices, the stored profiles including a geometry of surfaces of the wearable device, and sterilize and wirelessly charge the wearable device based at least partially on the profile.

4. An apparatus for sterilizing and charging a wearable device, comprising:

one or more light sources;

a wireless charging device configured to charge the wearable device; and a controller coupled to the one or more light sources and the wireless charging device and configured to:

determine, using the one or more light sources, that the wearable device is within an enclosure; and sterilize the wearable device using the one or more light sources; or wirelessly charge the wearable device using the wireless charging device; and a power source for providing power, wherein the wireless charging device is a wireless transmitter that wirelessly transmits a wireless charging signal, wherein to wirelessly charge the wearable device the controller is configured to:

determine a level of power of the wireless charging signal;

determine a spatial direction of the wireless charging signal to direct the wireless charging signal toward the wearable device; and emit the wirelessly charging signal to wirelessly charge a battery of the wearable device or operate the wearable device.

* * * * *